(12) United States Patent
Balsevich

(10) Patent No.: US 6,331,504 B1
(45) Date of Patent: Dec. 18, 2001

(54) SEED TREATMENTS FOR IMPROVING FALL SEEDING SURVIVAL OF CRUCIFERS

(76) Inventor: J. John Balsevich, 304 Lake Crescent, Saskatoon Saskatchewan (CA), S7H 3A2

(*) Notice: Subject to any disclaimer, the term of this patent is extended or adjusted under 35 U.S.C. 154(b) by 0 days.

(21) Appl. No.: 09/627,240

(22) Filed: Jul. 27, 2000

(30) Foreign Application Priority Data

Jul. 27, 1999 (CA) .................................................. 2278871

(51) Int. Cl.[7] ............................ A01N 43/16; A01N 31/02
(52) U.S. Cl. ............................ 504/100; 504/292; 47/57.6
(58) Field of Search ................................ 504/100, 292; 47/57.6

(56) References Cited

U.S. PATENT DOCUMENTS 5,661,111 * 8/1997 Kuramochi et al. ................ 504/284
5,797,976 * 8/1998 Yamashita ............................ 71/26

* cited by examiner

Primary Examiner—S. Mark Clardy
(74) Attorney, Agent, or Firm—J. Wayne Anderson

(57) ABSTRACT

Seeds of Brassica's and related species (Crucifers), having increased dormancy coupled with greater tolerance to stresses associated with fall seeding in long winter climates, are produced by treatment with solutions of sugars and/or polyols, for a specified period, typically 10 to 70 h at room termperature, followed by air drying to ambient moisture content. Dormancy is generally released on overwintering, moist chilling or hydration-dehydration-dehydration or as a function of increasing temperature or time or a combination of the preceding. Treated seeds afford better emergence over a larger seeding window for fall sown seeds of Brassicas and related species thus increasing the attractiveness of this practice for these crops.

20 Claims, 1 Drawing Sheet

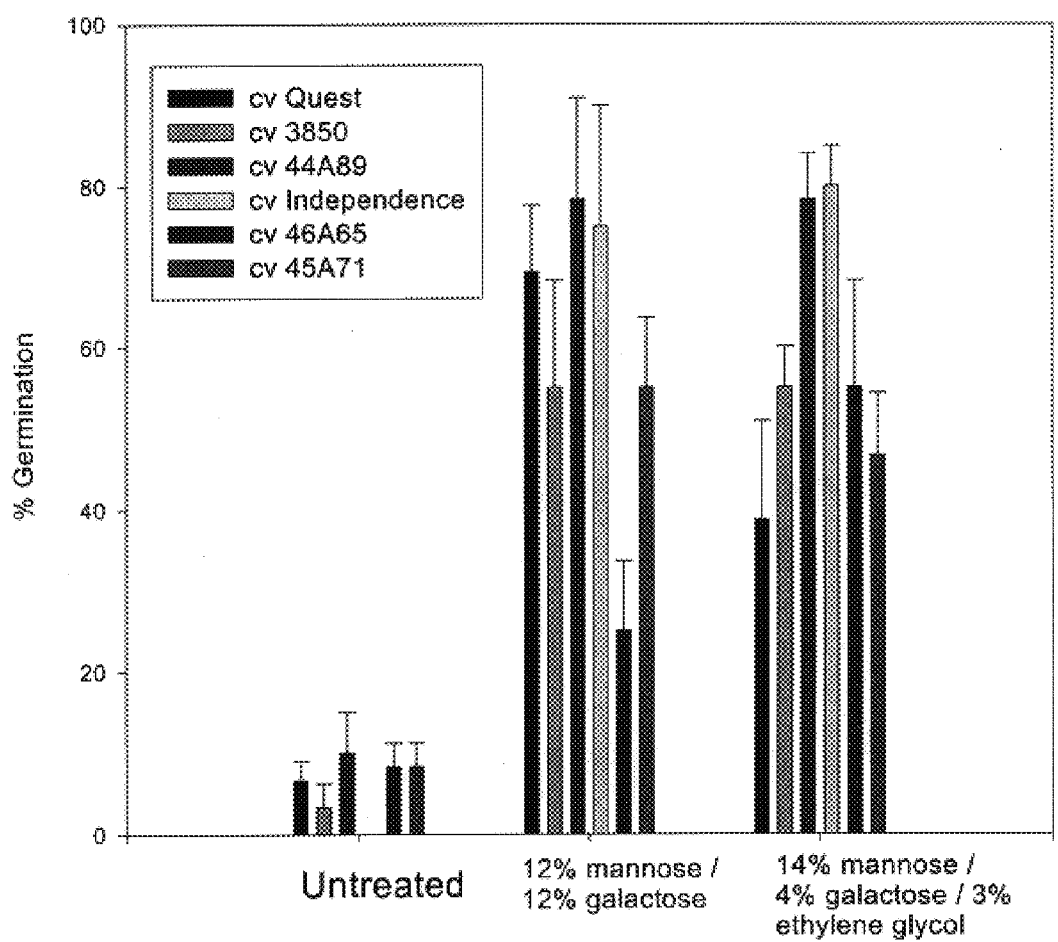

SEED TREATMENTS FOR IMPROVING FALL SEEDING SURVIVAL OF CRUCIFERS

This invention relates to a method and composition for enhancing spring emergence of fall seeded crucifers such as canola and mustard.

BACKGROUND OF THE INVENTION

For successful fall seeding, one needs a seed that remains dormant in the fall, survives the winter, and sprouts readily and vigorously in the spring—a difficult combination when every year is climatically different and soil types or conditions throughout the growing regions can vary considerably. Most crop plants being 'non-dormant', germinate readily over a wide range of temperatures in the presence of even small amounts of moisture.

Although most crop plants are 'non-dormant', germination is very species specific; some seeds require light, some darkness, some need a minimum temperature in the 20° C.'s, while others need cool temperatures to germinate. Some require vernalization or exposure to high heat.

Seeds possess germination and dormancy characteristics dependent on their genetic nature. Germination and dormancy vary radically among species. Germination occurs under specific environmental conditions with some variability. Seed of crop plants such as *Brassica napus* (*Argentine canola*), *B. rapa* (Polish canola), *B. juncea* (brown mustard) and *Sinapis alba* (yellow mustard) germinate within 4–5 days in the presence of suitable moisture at temperatures as low as 5° C., and within 24 hours as temperatures approach 20° C. The germination tends to be fairly consistent and these seeds are often referred to as being 'non-dormant'.[3]

There are instances where modification of the natural germination/dormancy characteristics of a species will have commercial applications. One potential application is in the area of fall seeding canola in cold winter, short summer growing areas such as the Canadian Prairies and northern United States. Fall seeding canola requires the seed to overwinter in the ground in the dormant state and emerge early in the spring prior to the time a producer can normally work the land. The benefits of fall seeding to the producer are numerous and include: spread of workload, maximum utilization of available soil moisture, and earlier maturity of up to 3 weeks. Yields and grade observed with successful fall seeded canola tend to be higher than with spring seeded crops. The main risk of fall seeding is loss of stand due to premature germination or poor spring vigor. A further drawback, aside from the risk, is the critical timing required for seeding. To be successful, seed must be sown into cold soil just prior to freeze-up, typically affording a window of only a few days. Any unexpected warming after sowing can lead to loss of the stand or poor emergence in the spring. As a consequence, fall seeding canola is currently practiced on a limited scale.

Seed sown in the fall can face numerous conditions which will challenge its subsequent viability in the spring, including fluctuating temperatures and moisture levels, which even if insufficient to induce germination, as exemplified by radicle emergence, may be sufficient to induce early germination-related events such as initiation of breakdown of reserves and structural polysaccharides which can result in poor emergence and vigor in the spring. The fluctuating temperature and moisture levels can also cause tissue damage due to hydration-desiccation after loss of desiccation tolerance, and freezing damage due to hydration followed by a freeze-thaw cycle. The further in advance of freeze-up that the seed is sown, the greater the risk of damage to the seed. To expand the window of opportunity for fall seeding and reduce the risk of loss of stand, all of these factors should be addressed.

Sugars can play an important role in these various processes. For example, respiration and growth of the embryo involve carbohydrate metabolism through the glucose and fructose phosphate pathways and the pentose phosphate pathway.[9] The initial softening up of the seed which reduces the physical barrier to radicle emergence involves hydrolysis of the galactomannan polymer cap and other polysaccharides.[14,15] Soluble sugars present in a seed can regulate internal osmotic pressures which may affect the amount of moisture required for germination to proceed. In addition, soluble sugars can play a role in stabilizing membranes subjected to desiccation and freezing stresses.[10-13]

Seeds normally contain a small amount of soluble sugars, typically polysaccharides such as raffinose or monosaccharides such as glucose, although the amount and type is dependant upon the species, and although, addition of sugars or related derivatives to a seed might be expected to affect various properties such as germination, dormancy, seedling vigor, and possibly tolerance to desiccation and freezing, the concept that treatment of canola or related species seed with appropriate sugar solutions would result in that seed being made more suitable for fall sowing in long winter regions is not initially obvious or a priori predictable.

The basic concept that making a 'non-dormant' seed less germinable would result in improving its fall seeding was also not a 'given'. Originally when abscisic acid and analogs or other known germination inhibitors such as coumarin were investigated, inhibition of germination in the lab was observed, but improved fall seeding emergence in the field was not. Although increased dormancy may be one factor to consider for fall seeding, the survival of the seed over the winter and the ready and vigorous emergence of the fall-sown seed in the spring are crucial and it would appear may be negatively impacted by some dormancy enhancing treatments.

DESCRIPTION OF THE PRIOR ART

'Priming' seeds is a process previously described in the public domain and several patents which involves controlled hydration of seeds to a level that permits pregerminative metabolic activity but not actual germination. The process consists of bathing seeds in aqueous solutions having a high osmotic potential or hydrating seeds with a measured quantity of water, insufficient to cause germination. Solutions of high osmotic potential are (generally obtained using compounds such as polyethylene glycol 4000, although inorganic salts, and mannitol have also been used. 'Priming' has been performed to synchronize germination, speed germination, or to study the effects of water potential on germination.[1,2]

U.S. Pat. No. 3,803,761 describes a method for coating seeds with polymeric material which acts as a physical barrier to moisture, thus delaying germination. This invention is directed to a plant seed having a coating of a polymer material, said material in film form permitting oxygen transmission sufficient for normal respiration of the seed and having a controlled permeability to water and an elongation to breaking less than about 200 per cent and said coating being of thickness that it will control the water imbibation of the seed to the extent necessary to delay germination until environmental conditions are satisfactory to continued crop growth.

U.S. Pat. No. 5,294,593 describes a method for inducing dormancy in 'non-dormant' seed of lettuce, pepper, tomato, carrot, onion, impatiens, and primrose using a solution of giberellin synthesis inhibitor, preferably tetcyclis.

U.S. Pat. Nos. 5,518,995 and 5,201,931 describe the use of synthetic analogs of the plant hormone abscisic acid to modify germination characteristics of seeds.

It is noted that as far as we are aware, none of these prior art treatments have been used for fall seeding crucifers.

SUMMARY OF THE INVENTION

This invention relates to adding water-soluble sugars essentially including mannose and/or derivatives or mimics thereof, and optionally polyols, to the seeds of crucifers, so that germination- and stress tolerance-related properties are affected in such a way as to make the seeds more suitable for fall sowing, i.e. by slowing germination while increasing tolerance to desiccation and freezing stresses thus resulting in greater emergence and survival in the spring and allowing a larger seeding window in the fall.

One problem of fall seeding is that canola and most crop plants are 'non-dormant' and so fall seeding has been practiced on a limited scale by seeding the 'day before winter'. Non-dormant is a relative term as canola seed doesn't germinate at low temperatures—typically below 5 deg C, but this 'base' temperature varies somewhat with different cultivars and species (eg for canola typically between 3 & 6 deg C) and of course a population of seed of the same cultivar contains some seed which will germinate below a given temperature.

Enhancing dormancy to improve fall seeding is only half the battle—the other half is to obtain good germination after overwintering in the field with the seedling possessing sufficient vigor to survive the challenge of frosts, insects, fungi, and drought.

Other similar crops for which the treatment appears to work are the mustards (brown mustard=*Brassica juncea*, yellow mustard=*Sinapis alba*, and *Brassica carinata*) and by extension to crucifers in general.

According to one aspect of the invention, a method is provided for enhancing spring emergence of fall seeded crucifers, comprising exposing the seed to an aqueous treatment solution comprising 5–30% by volume of a water-soluble sugar or sugar mixture, including mannose and/or derivatives or mimics thereof, and optionally polyols, for a time sufficient for absorption of the solution by the seed, but insufficient for germination of the seed to occur, followed by drying of the seed to ambient moisture content. This treatment may be repeated several times to produce the required characteristics.

According to another aspect of the invention, a method for treating plant seed is provided, comprising (a) exposing the seed to an aqueous treatment solution for a time sufficient for absorption of the solution by the seed, but insufficient for germination of the seed to occur, (b) drying the seed to ambient moisture content, (c) re-exposing the seed to an aqueous treatment solution for a time sufficient for absorption of the solution by the seed, but insufficient for germination of the seed to occur, and (d) re-drying the seed to ambient moisture content.

According to a further aspect of the invention, a composition for treating plant seeds is provided, comprising an aqueous solution comprising 5–30% w/v of a water-soluble sugar or a sugar mixture, including mannose and/or a derivative or a mimic thereof.

According to yet another aspect of the invention, a composition for treating plant seeds is provided, comprising mannose (11±4% w/v), galactose (6±6% w/v), ethylene glycol (3±3% w/v), other sugars (0–5% w/v), and the balance to 100% being water.

Further, the method of soaking the seed with a sugar solution (containing mannose) although superficially similar to priming (mentioned above) is completely different. Priming is generally accomplished by two methods, the first, by treating seeds with a measured and limited (ie less than necessary for germination) amount of water so that 'normal' germination activity is initiated but only to a limited extent, such that the seed doesn't actually germinate (ie its radicle has not broken through the seed coat) but is 'ready and "raring" to go' as soon as it is exposed to more moisture— the second method of priming is to soak the seed in an excess of solution containing a sufficient amount of osmoticum (which prevents germination) which allows the seed to abosorb a limited amount of moisture but not to geminate, thus being equivalent to the first method by a slightly different means. The osmotica used are generally polymers which do not enter the seed (due to their size) specifically because a modification of 'normal' metabolism is unwanted. Mannitol and various inorganic salts have been used previously as osmotica but their use has generally been usurped by such polymers as polyethylene glycol 4000 (av mol wt of 4000) because of concern over the possibility of altering 'normal' seed metabolism.

The methods according to the present invention use exposure of seeds to sugar solutions, not to initiate normal germination events, but to introduce sugars into the seed which will modify the normal metabolic events. Primed seeds germinate quicker and more evenly than unprimed seeds—seeds 'treated' with appropriate sugar solutions according to the present invention germinate more slowly than untreated seeds and survive desiccation-dehydration stress better.

Mannose and sources thereof include hydrolysates derived from guar, cassia etc gums or mannans, such as spent coffee grounds.[6] Also, here are sugars which mimic mannose, e.g. 2-deoxyglucose and glucosamine to name two, as well as derivatives such as mannose methyl (ethyl, propyl, etc:) glycoside which are expected to be equivalent in action. The 2-deoxyglycoside is very expensive and not practical as a substitute. Glucosamine treated seed exhibited root tip damage on germination, indicative of some toxicity effect of that sugar. Regarding polyols, sugar alcohols of the general formula $C_nH_{n+x}(OH)_n$, where n=2–6 and x=2, or n=6 and x=0. Appear to increase dormancy and complement the use of various sugar solutions.

One specific method involves making up a solution of sugars/polyols generally containing 5% to 30% sugars/polyols (w/v), and adding 50 ml to 300 ml of this solution to 1 kg of seed, followed by mixing to ensure even exposure, standing for 20 to 70 hours at 22° C. in a closed environment, and subsequently drying in air to ambient moisture levels as determined by a return of seed weight to stable levels. The greater the length of time the greater the dormancy of the treated seed. The seed can be treated again in a similar manner to increase dormancy further. Rinsing of seed with water prior to air drying will remove any residual sugars/polyols on the seed surface, but is not essential.

The treatment solution may also contain an antimicrobial/antifungal agent or a preservative. Alternatively, a coating of the antimicrobial/antifungal agent or preservative rmay be applied afterwards, or may be already present on the seed.

Another method involves exposing seed to excess sugar/polyol solution (typically >1.5 volumes of solution per wt of seed, ie 1.5 l per 1 kg), removing the excess solution after 10 to 30 hours at 22° C., rinsing seed with water and air drying to stable weight.

The sugar/polyol solutions can vary widely in their composition but generally include 7–15% w/v of mannose and/or a derivative or mimic thereof, and may contain other monosaccharides e.g. glucose and/or polysaccharides and may further contain polyhydric alcohols. Examples of such compounds include ethylene glycol, glycerol, xylitol, sorbitol, mannitol, fructose, glucose, arabinose, galactose, xylose, sucrose, maltose, hydrolysates of mannans, galactomannans, arabinogalactans, xylans, and in addition may contain various other sugars and polyols.

Hydrolysates refer to mixtures of monosaccharides obtained via hydrolysis of polysaccharides by chemical or enzymatic means. For example, guar gum, cassia gum, locust bean gum, xanthan gum and acacia gums were hydrolyzed by adding the dry powdered gums to a hot, stirred solution of 0.5 M sulfuric acid, typically 100 gm of gum to 1 litre of aqueous acid for 1 to 20 hours. The acid hydrclysate is cooled and neutralized with calcium carbonate and filtered to remove insolubles. Excess calcium ions are removed by treatment with some oxalic acid, typically 1 gm, and potassium hydroxide, typically 0.5 gm, followed by filtration, deionization and neutralization by passage through a strong acid polystyrene resin and a weak base polystyrene resin, respectively. The resultant solution is generally concentrated by evaporation to ca 50% (w/v) or greater for storage. The concentrated hydrolysate is then diluted appropriately for use in the various formulations.

BRIEF DESCRIPTION OF THE DRAWING

The FIGURE is a graph illustrating the germination/survival of several canola cultivars after simulated fall planting.

DETAILED DESCRIPTION OF THE INVENTION

Mannose is a relatively rare sugar which, however can conveniently be obtained from hydrolysis of inexpensive and readily available galactomannans such as guar, cassia, and locust bean gums.[6] Another potential inexpensive source of mannose may be spent coffee grounds which contain mannans and glucomannans and which on hydrolysis yield mixtures rich in mannose plus significant quantities of glucose. Investigations were based predominantly on galactomannan hydrolysates (mannose/galactose mixtures) because this is the most likely source of the quantities of material required on commercialization. Regarding commercialization, the use of non-toxic guar or related gums as a feed-stock and the use of naturally occurring sugars for the treatment should not require extensive toxicology, or environmental assessment. 3 kg of seed are used for seeding 1 acre of land and this amount of seed will probably have been treated with 50–100 gm of sugars, most of which will be metabolized and used by the seed on germination.

Mode of Action

The mode of action is believed to be due to a combination of four possible effects, based on what is known in the literature.

1. I believe the dominant mode of action is based on the absorption of mannose into the seed and its action as an inhibitor of respiration due to its competion with glucose for 6-phosphorylation by hexokinase. The formed mannose-6-phosphate also is a hexokinnase inhibitor and also ties up some of the inorganic phosphate necessary for germination and growth of the embryo. There is a long history of mannose being a growth and germination inhibitor and there appears at least one reference on galactose as a growth inhibitor.[4,5,6,8]

Having made a case for mannose, however, the amount of galactose (or other sugars) present, as well as the presence of polyols, appears to affect germination/dormancy characteristics, as well as survival in simulated fall seeding assays. The reason for this is that respiration and sugar metabolism in seeds is a complex process involving many enzymatic pathways, some of which are interlinked. Adding various sugars and polyols or altering their ratios will likely modify some enzyme activities and the flow of various endogenous intermediates through the natural pathways significantly. It is thus likely that modification of respiration of the embryo by the sugar/polyols in the formulation is responsible for increasing the dormancy of the seeds in a manner appropriate for fall seeding—however not all compositions produce the same type of dormancy. The affect of modifying ratios of components or changing sugars in the composition was not a priori evident, and the positive effects on fall seeding were also not evident until after some attainment of field data.[7,9]

2. A second possible mode of action resulting in increased dormancy due to mannose and galactose and to a lesser extent other sugars may be as a consequence of the inhibition of some of the hydrolytic enzymes involved in breaking down reserve and structural polysaccharides of the seed. It is possible that monsaccharides act as end-product feed-back inhibitors to polysaccharide hydrolytic enzymes (ie they stop the softening up of the seed by the hydrolytic enzymes).[14,15]

3. The third possible beneficial mode of action of sugars on seeds sown in the fall is the stabilization of membranes by the sugars, thus resulting in reduced membrane damage from freezing and/or desiccation stresses.[10-13]

4. The fourth possible mode of action is that by the addition of water-soluble sugars in the seed, a higher level of moisture will be required for germination due to the inhibitory effect that solutions of high osmotic potential have. The increased soluble sugars in the treated canola seeds are detectable by chromatographic analysis of the washed, ground up seeds.

From a commercial point of view, the most effective way to treat the seeds would appear to be to evenly apply e.g. by spray or mixing, a limited volume of the treatment solution (typically 50–300 ml per kg of seed), comprising mannose (11±4% w/v), galactose (6±6% w/v), ethylene glycol (3±3% w/v), other sugars (0–5% w/v), possibly containing a preservative, with the seed and to let it soak or imbibe in over a 24 to 48 hour period of time in a closed container at room temperature, followed by air drying to constant weight. As an aside, the treated seed should be coated with a commercial fungicide coating such as "Premier Plus"™, "Vitavax"™, "Foundation"™ or others prior to seeding—although most of the trials were performed with uncoated seed, it has been observed that using a commercial fungicide coating results in a significant improvement in emergence.

The present invention will be more readily illustrated by referring to the following examples which are introduced only to illustrate rather than limit the scope of the present disclosure.

EXAMPLE 1

Effect of various treatment solutions of sugars and/or polyols on the germination of various species of Crucifers and the effect of the treatments on desiccation tolerance as determined by a hydration-desiccation-rehydration assay.

Assays done in triplicate with 20–25 seeds per 90 mm Petri dish using two Whatman no. 1 filter papers wetted with 3 ml of water. Desiccation tolerance assays were performed as for germination assys but by allowing seed to imbibe water for 2 days followed by drying in air for two days. Germination/survival was then determined by re-wetting seeds (3 ml/Petri dish) and observing for up to 6 days to obtain survival numbers.

TABLE 1

| No. | Species | Variety and/or Cultivar | Treatment solution, w/v (Treatment = >2 ml of solution per gram of seed, 24 h at 22 deg C. Solutions contain 0.005% benzoic acid and 0.005% 8-hydroxyquinoline, w/v, as preservative) | Hours to 50% Germination at 22 deg C. | % Maximum Germination | % Germination/ Survival after hydration-desication-rehydration |
|---|---|---|---|---|---|---|
| A | B. napus | Quest | none (untreated seed) | 24 | 96 | 3 |
| B | B. juncea | Cutlass | None | 20 | 93 | 7 |
| C | B. carinata | S67 | None | 18 | 90 | 1 |
| D | B. rapa | 41P55 | None | 32 | 87 | 18 |
| E | Sinapis alba | Pennant | None | 13 | 93 | 0 |
| F | B. oleracea (broccoli) | Botrytis cv Green Sprouting | None | 24 | 90 | 7 |
| G | B. oleracea (brussels sprout) | Gemmifera cv Long Island Improved | None | 40 | 87 | 7 |
| H | B. oleracea (cauliflower) | Botrytis cv Super Snowball | None | 24 | 88 | 5 |
| I | B. napus | Quest | 15% mannose | >120 | 58 | 62 |
| J | | Quest | 15% lactose | 40 | 94 | 85 |
| K | | Quest | 15% galactose | 105 | 70 | 92 |
| L | | Quest | 15% arabinose | 96 | 82 | 45 |
| M | | Quest | 15% glucose | 75 | 84 | 80 |
| N | | Quest | 15% fructose | 90 | 82 | 90 |
| O | | Quest | 5% glucosamine HCl | >120 | 32 | 92 |
| P | | Quest | 15% mannitol | 100 | 80 | 62 |
| Q | | Quest | 10% ethylene glycol (v/v) | >120 | 51 | 33 |
| R | | Quest | 7.5% mannose, 7.5% lactose | >120 | 42 | 72 |
| S | | Quest | 7.5% mannose, 7.5% galactose | 110 | 78 | 57 |
| T | | Quest | 7.5% glucose, 7.5% fructose | 65 | 84 | 65 |
| U | | Quest | 7.5% lactose, 7.5% mannitol | 48 | 90 | 70 |
| V | | Quest | 14% mannose, 4% galactose, 3% ethylene glycol, v/v | >120 | 76 | 92 |
| W | | Quest | 12% mannose, 12% galactose | 90 | 88 | 90 |
| X | | Quest | 18% maltose | 40 | 94 | 45 |
| Y | | Quest | 30% sucrose | 60 | 82 | 65 |
| Z | B. juncea | Cutlass | 22% guar gum hydrolysate | 60 | 91 | 92 |
| AA | B. juncea | Cutlass | 18% cassia gum/guar gum (2:1) hydrolysate, 2.8% ethylene glycol | 80 | 93 | 95 |
| BB | B. carinata | S67 | 22% guar gum hydrolysate | 70 | 80 | 70 |
| CC | B. carinata | S67 | 18% cassia gum/guar gum (2:1) hydrolysate, 2.8% ethylene glycol | 80 | 78 | 67 |
| DD | B. oleracea (broccoli) | Botrytis cv Green Sprouting | 18% cassia gum/guar gum (2:1) hydrolysate, 2.8% ethylene glycol | 80 | 83 | 82 |
| EE | B. oleracea (brussels sprout) | Gemmifera cv Long Island Improved | 5% glycerol, 2.5% ethylene glycol | >120 | 70 | 63 |
| FF | B. oleracea (cauliflower) | Botrytis cv Super Snowball | 5% glycerol, 2.5% ethylene glycol | >120 | 73 | 75 |

TABLE 1-continued

| No. | Species | Variety and/or Cultivar | Treatment solution, w/v (Treatment = >2 ml of solution per gram of seed, 24 h at 22 deg C. Solutions contain 0.005% benzoic acid and 0.005% 8-hydroxyquinoline, w/v, as preservative) | Hours to 50% Germination at 22 deg C. | % Maximum Germination | % Germination/ Survival after hydration-desiccation-rehydration |
|---|---|---|---|---|---|---|
| GG | B. rapa | 41P55 | 14% mannose, 4% galactose, 3% ethylene glycol, v/v | >120 | 73 | 55 |
| HH | B. rapa | 41P56 | 12% mannose, 12% galactose | >120 | 82 | 65 |

In general, Table 1 shows that the treatment of Crucifer seeds with various sugar/polyol solutions afforded a more dormant seed, as exemplified by a longer time to 50% germination, and a more desiccation-tolerant seed, as exemplified by the higher survival rate after hydration-desiccation-rehydration.

EXAMPLE 2

Germination/survival of several herbicide-tolerant (HT) cultivars of canola (B. napus) after simulated fall planting is illustrated in the FIGURE . Simulated fall planting performed in triplicate, by placing 20–25 seeds on wefted (3.5 ml water) Whatman filter paper (2 pieces of no. 1) in Petri dishes (90 mm) at 10° C. for 1–3 days, 5° C. for 2–4 days, 0° C. for 1 day, −13 to −15° C. for 4–9 days, followed by warming to 22° C. and checking for germination and survival after a further 7 days. The treatments did not show any cultivar discrimination.

EXAMPLE 3

Germination/survival after simulated fall seeding at three moisture levels of seed treated with limited amount of treatment solution, typically, 1 ml of solution per 5 gm of seed for 40 to 50 h followed by air drying to stable moisture content/weight. Experiments were performed in triplicate, sd=standard deviation. Simulated fall seeding performed with 20–25 seeds per 9 cm Petri dish, containing 2 Whatman no. 1 filter papers treated with 1.8, 2.7 and 3.6 ml of water. Seeds were maintained at 10° C. for 1 day, 4° C. for 3 days, 0° C. for 1 day, and −14° C. for 5 days, then warmed to ambient temperature and gemination/survival measured after 6 days. Seeds used were B. napus cv 45A71. Treatment solutions contained 0.005% benzoic acid/0.005% 8-hydroxyquinoline and/or 0.1% sulfur as antimicrobial agents.

TABLE 2

| | | $H_2O$ | | | | | |
|---|---|---|---|---|---|---|---|
| | | 1.8 ml | | 2.7 ml | | 3.6 ml | |
| | | % Germination/Survival | | | | | |
| # | Treatment composition (% w/v) | ave | sd | ave | sd | ave | sd |
| V-1 | 12% fructose, 3% ethylene glycol | 28 | 16 | 48 | 33 | 22 | 23 |
| V-2 | 8% fructose, 8% xylose | 15 | 9 | 40 | 35 | 27 | 33 |
| V-3 | 12% fructose, 3% sorbitol | 23 | 24 | 43 | 38 | 33 | 10 |
| V-4 | 8% fructose, 4% guar gum hydrolysate, 2% mannose | 35 | 0 | 42 | 28 | 28 | 26 |
| V-5 | 15% xylose | 37 | 2 | 52 | 23 | 20 | 17 |
| V-6 | 6% fructose, 6% xylose, 2% arabinose | 25 | 18 | 42 | 32 | 22 | 21 |
| V-7 | 12% xylose, 3% sorbitol | 40 | 30 | 32 | 26 | 17 | 10 |
| V-8 | 6% fructose, 6% guar gum hydrolysate, 3% xylose | 20 | 17 | 30 | 10 | 42 | 38 |
| V-9 | 8% fructose, 8% guar gum hydrolysate | 10 | 9 | 37 | 28 | 3 | 3 |
| V-10 | 9% guar gum hydrolysate, 6% xylose | 17 | 25 | 17 | 29 | 8 | 14 |
| V-11 | 12% xylose, 3% ethylene glycol | 33 | 23 | 25 | 23 | 20 | 26 |
| V-12 | 10% guar gum hydrolysate, 6% arabinose | 32 | 25 | 73 | 12 | 45 | 17 |
| V-13 | 16% guar gum hydrolysate, 4% sorbitol | 38 | 16 | 62 | 12 | 57 | 36 |
| V-14 | 9% mannose, 4% galactose, 3% dulcitol | 35 | 30 | 45 | 9 | 28 | 33 |
| V-15 | 12% arabinose, 3% sorbitol | 27 | 13 | 17 | 25 | 30 | 30 |
| V-16 | 6% fructose, 6% guar gum hydrolysate, 3% ethylene glycol | 40 | 5 | 10 | 0 | 37 | 28 |
| V-17 | 6% fructose, 6% guar gum hydrolysate, 3% sorbitol | 48 | 10 | 57 | 10 | 28 | 6 |
| V-18 | 6% fructose, 6% guar gum hydrolysate, 3% mannitol | 53 | 15 | 57 | 8 | 7 | 12 |
| V-19 | 5% fructose, 6% guar gum hydrolysate, 3% ethylene glycol, 3% mannose | 33 | 18 | 28 | 13 | 15 | 13 |

TABLE 2-continued

| | | H$_2$O | | | | |
| | | 1.8 ml | | 2.7 ml | | 3.6 ml | |
| | | % Germination/Survival | | | | | |
| # | Treatment composition (% w/v) | ave | sd | ave | sd | ave | sd |
| --- | --- | --- | --- | --- | --- | --- | --- |
| V-20 | 6% fructose, 2% guar gum hydrolysate, 6% arabinose, 2% galactose | 43 | 20 | 65 | 9 | 8 | 10 |
| V-21 | 16% guar gum hydrolysate, 3% xylitol | 40 | 31 | 22 | 21 | 55 | 28 |
| V-22 | 18% acacia gum hydrolysate | 22 | 20 | 57 | 19 | 23 | 21 |
| V-23 | none (untreated) | 37 | 30 | 16 | 21 | 9 | 11 |
| V-24 | Water & 0.005% benzoic acid/0.005% 8-hydroxyquinoline | 18 | 24 | 17 | 20 | 5 | 9 |

Table 2 shows that treated seed generally afforded improved survival, indicative of protection to freezing stress, particularly at higher moisture levels. Initial field trial results however indicated that best results were obtained with mannose containing treatments.

EXAMPLE 4

Emergence results from various field trials with treated and untreated seed of various species and cultivars.

TABLE 3

Garden Plot, Saskatoon, Sk -- % Emergence (Apr. 28, 1999) -- single rows, 200 seeds/row

| Date seeded | Untreated | 20% Guar Gum Hydrolysate (excess) | 18% - Cassia Gum/ Guar Gum (3:1) Hydrolysate, 3% ethylene glycol (excess) |
| --- | --- | --- | --- |
| A) *Sinapis alba* cv Pennant | | | |
| Oct. 29, 1998* | 0 | 20 | 26 |
| B) *Brassica carinata* cv S67 | | | |
| Oct. 26,1998* | 1 | 29 | 16 |

| Date seeded | Untreated | 20% Guar Gum Hydrolysate - (excess, drip method**) | 18% - Cassia Gum/ Guar Gum (3:1) Hydrolysate/3% ethylene glycol - (excess) |
| --- | --- | --- | --- |
| C) *Brassica napus* cv 45A71 | | | |
| Oct. 22, 1998* | 2 | 3 | 31 |

| Date seeded | Untreated | 1:1 Mixture of treated seeds (20% Guar Gum Hydrolysate and 18% - Cassia Gum/Guar Gum (3:1) Hydrolysate/3% ethylene glycol | 18% - Cassia Gum/ Guar Gum (3:1) Hydrolysate/3% ethylene glycol - (excess, drip method**) |
| --- | --- | --- | --- |
| Oct. 22,1998* | 2 | 14 | 25 |

*October 1998 was a wet warm month. Seeding was done into wet soil on sunny warm days (maximum daytime temp, 14–20° C.) -- not normally recommended for fall seeding. Although the emergence rates were rather low, the treated seed clearly outperformed the untreated seed. Plants began emerging on Apr. 12, 1999.

TABLE 3-continued

**Drip method consisted of dripping treatment solution onto seeds, allowing it percolate though seeds then recycling collected solution onto seeds. Generally the batch method, which consisted of placing seed and excess solution in a closed container for approximately 20–24 h. Both methods were followed by a water rinse and air drying to constant weight.

Garden Plot, Saskatoon, Sk -- % Emergence (May 1, 1998) -- single rows, 200 seeds/row (seeds treated with excess solution for 24h - batch method)

| Date seeded | Untreated | 12% mannose/ 12% galactose | 14% mannose/ 4% galactose/ 3% ethylene glycol | 6% mannose/ 3% galactose/ 10% sucrose/ 2% glycerol/ 2% ethylene glycol |
| --- | --- | --- | --- | --- |
| D) *B. napus* cv Quest | | | | |
| Oct. 16, 1997 | 0 | 20 | 17 | not done |
| Oct. 22, 1997 | 16 | 31 | 42 | 33 |

| Date seeded | Untreated | 12% mannose/ 12% galactose | 14% mannose/ 4% galactose/3% ethylene glycol |
| --- | --- | --- | --- |
| E) Scott, Sk, small plot (stubble), random block (4 replicate) -- emergence (plants/sq. m. ± sd). May 25 1998 (Seeds treated with excess solution for 20–24 h - batch method) | | | |
| Oct. 14, 1997* | 7 ± 6.9 | 12 ± 1.7 | 15 ± 8.5 |
| Oct. 22, 1997 | 15 ± 5.6 | 26 ± 13.9 | 20 ± 5.2 |
| Oct. 26, 1997 | 22 ± 13.2 | 30 ± 8.3 | 22 ± 12.5 |
| Nov. 4, 1997 (freeze up) | 28 ± 14.0 | 27 ± 13.3 | 25 ± 8.0 |

*1997 was an El Nino year and was characterized by a very dry and mild October and November References 1. Enhancement of Canola Seed Germination and Seedling Emergence at Low Temperature by Priming. G. -H. Zheng, R. W. Wilen, A. E. Slinkard, and L. V. Gusta. Crop Science. 1994. Vol. 34, p. 1589–1593.
2. Effect of Osmotic Priming on Germination Characteristics of Celeriac (*Apium graveolens L. var. rapaceum*). R. L. K. Drew and J. Dearman. Seed Sci. & Technol. 1993. Vol. 21, p. 411–415.
3. The Physiology and Biochemistry of Seed Dormancy and Germination. A. A. Khan Editor, 1977. North Holland, Amsterdam.—general reference on germination.
4. Inhibition of germination by glucose analogues that are hexokinase substrates. N. K. Matheson and D. K. Myers. Phytochemistry. 1998. Vol. 48, p. 241–248.
5. Inhibition of Pear Fruit Ripening by Mannose. C. B. Watkins and C. Frenkel. Plant Physiol. 1987. Vol 85, p. 56–61.

6. Mannose and Green Plants: Occurrence, Physiology, Metabolism, and Use as a Tool to Study the Role of Orthophosphate. A. Herold and D. H. Lewis. New Phytol. 1977. Vol 79, p. 1–40.

7. Galactose-induced Ethylene Evolution in Mung Bean Hypocotyls: A Possible Mechanism for Galactose Retardation of Plant Growth. G. C. Colclasure and J. H. Yopp. Physiol. Plantarum. 1976. Vol. 37, p. 298–302.

8. Mannose as a Metabolite and an Inhibitor of Metabolism in Euglena. J. J.

Fungal Polyol Metabolites in the Control of Carbohydrate Metabolism of Mycorrhizal Roots of Beech. R. T. Wedding and J. L. Harley. New Phytol. 1976. Vol. 77, p. 675–688.

Introduction of Specific Carbohydrates into Eucalyptus Gunnii Cells Increases their Freezing Tolerance. N. LeBorgne, C. Teulieres, S. Travert, M. -P. Rols, J. Teissie, and A. M. Boudet. 1995. Eur. J. Biochem. Vol. 229, p. 710–717.

Sugars and Desiccation Tolerance in Seeds. K. L. Koster and A. C. Leopold. Plant Physiol. 1988. Vol. 88, p. 829–832.

Effects of Carbohydrates on Membrane Stability at Low Water Activities. L. M. Crowe, R. Mouradian, S. A. Jackson and C. Womersley. 1984. Biochim. Et Biophys. Acta. Vol. 769, p. 141–150.

Prevention of Fusion and Leakage in Freeze-dried Liposomes by Carbohydrates. 1986. Biochim et Biophys. Acta. Vol. 861, p. 131–140.

Liberating the Radicle: A Case for Softening Up. M. Black. 1996. Seed Science Research. Vol. 6, 39–42.

Development of Galactomannan-hydrolyzing Activity in the Micropylar Endosperm Tip of Tomato Seed Prior to Germination. M. Nomaguchi, H. Nonagaki and Y. Morohashi. 1995. Physiol. Plantarum. Vol. 94, p. 105–109.

We claim:

1. A method for enhancing spring emergence of fall seeded crucifers, comprising
   (a) exposing the seed to an aqueous treatment solution comprising 5–30% w/v of a water soluble sugar, selected from the group consisting of mannose, a mannose derivative, a mixture of mannose and a mannose derivative, a mixture of mannose and another water-soluble sugar, a mixture of a mannose derivative and another water-soluble sugar, and a mixture of mannose, a mannose derivative and another water-soluble sugar, for a time sufficient for absorption of the solution by the seed, but insufficient for germination of the seed to occur, and
   (b) drying the seed to ambient moisture content.

2. A method according to claim 1, wherein the treatment solution includes the water-soluble sugar in an amount of 7.5–15% w/v.

3. A method according to claim 1, wherein the treatment solution comprises 7.5–14% w/v of mannose and 4–12% w/v of galactose.

4. A method according to claim 1, wherein the treatment solution comprises 7.5–12% w/v of mannose and 7.5–12% w/v of galactose.

5. A method according to claim 1, wherein the treatment solution comprises 12% w/v of mannose and 12% w/v of galactose.

6. A method according to claim 2, wherein the treatment solution additionally comprises an alcohol of the formula $C_n H_{n+x}(OH)_n$ wherein n=2 to 6 and x=2, or n=6 and x=0.

7. A method according to claim 6, wherein the alcohol is ethylene glycol.

8. A method according to claim 7, wherein the treatment solution comprises 14% w/v of mannose, 4% w/v of galactose and 3% w/v of ethylene glycol.

9. A method according to claim 2, wherein the treatment solution comprises a galactomannan or mannan hydrolysate.

10. A method according to claim 1, wherein the treatment solution further comprises a fungicide an antimicrobial agent, or a preservative.

11. A method according to claim 1, including the additional steps of
   (a) re-exposing the seed to the aqueous treatment solution for a second time sufficient for absorption of the solution by the seed, but insufficient for germination of the seed to occur,
   (b) re-drying the seed to ambient moisture content.

12. A method according to claim 1 wherein the crucifer is canola.

13. A method for treating plant seed, comprising (a) exposing the seed to an aqueous treatment solution for a time sufficient for absorption of the solution by the seed, but insufficient for germination of the seed to occur, (b) drying the seed to ambient moisture content, (c) re-exposing the seed to an aqueous treatment solution for a time sufficient for absorption of the solution by the seed, but insufficient for germination of the seed to occur, and (d) re-drying the seed to ambient moisture content.

14. A composition for treating plant seed, comprising 5–30% w/v of a water soluble sugar, selected from the group consisting of mannose, a mannose derivative, a mixture of mannose and a mannose derivative, a mixture of mannose and another water-soluble sugar, a mixture of a mannose derivative and another water-soluble sugar, and a mixture of mannose, a mannose derivative and another water-soluble sugar, and an alcohol of the formula $C_n H_{n+x}(OH)_n$, wherein n=2 to 6 and x=2, or n=6 and x=0.

15. A composition according to claim 14, including the water-soluble sugar in an amount of 7.5–15% w/v.

16. A composition according to claim 14, comprising 7.5–14% w/v of mannose and 4–12% w/v of galactose, the balance to 100% being water.

17. A composition according to claim 14, comprising 7.5–12% w/v of mannose and 7.5–12% w/v of galactose, the balance to 100% being water.

18. A composition according to claim 14, comprising 12% w/v of mannose and 12% w/v of galactose, the balance to 100% being water.

19. A composition according to claim 14, comprising mannose . . . 11±4% w/v galactose . . . 6±6% w/v ethylene glycol . . . 3±3% w/v other sugars . . . 0±5% w/v water . . . balance to 100%.

20. A composition according to claim 14, comprising 14% w/v of mannose, 4% w/v of galactose and 3% w/v of ethylene glycol.

* * * * *